United States Patent
Noonan

(10) Patent No.: US 10,117,960 B2
(45) Date of Patent: Nov. 6, 2018

(54) AIR TREATING APPARATUS FOR PET SANITARY STATION AND METHODS OF MOUNTING AND DOSING SAID APPARATUS

(71) Applicant: Wallace Noonan, Allentown, NJ (US)

(72) Inventor: Wallace Noonan, Allentown, NJ (US)

( * ) Notice: Subject to any disclaimer, the term of this patent is extended or adjusted under 35 U.S.C. 154(b) by 304 days.

(21) Appl. No.: 15/330,416

(22) Filed: Sep. 19, 2016

(65) Prior Publication Data

US 2018/0078667 A1   Mar. 22, 2018

(51) Int. Cl.
*A01K 1/01*   (2006.01)
*A61L 9/12*   (2006.01)

(52) U.S. Cl.
CPC .............. *A61L 9/12* (2013.01); *A01K 1/0107* (2013.01)

(58) Field of Classification Search
CPC ................................ A61L 9/12; A01K 1/0107
See application file for complete search history.

(56) References Cited

U.S. PATENT DOCUMENTS

| | | |
|---|---|---|
| 1,384,866 A | 7/1921 | Silvers |
| 3,428,026 A | 2/1969 | Sohmers |
| 3,793,989 A | 2/1974 | Clark |
| 3,872,832 A | 3/1975 | Quinn |
| 4,090,470 A | 5/1978 | Williams |
| 4,305,544 A | 12/1981 | Noonan |
| 5,129,364 A * | 7/1992 | Pirkle .................. A01K 1/0125 119/167 |
| 5,220,885 A | 6/1993 | Goetz |
| 5,289,800 A | 3/1994 | Walton |
| 5,961,043 A * | 10/1999 | Samuelson ......... A01M 1/2044 206/486 |
| 6,168,088 B1 | 1/2001 | Mobley |
| 7,594,480 B2 | 9/2009 | Cressy |
| 8,864,744 B2 | 10/2014 | Noonan |
| 2004/0000599 A1* | 1/2004 | Cuthbert ............ A45D 40/0087 239/327 |
| 2011/0147478 A1* | 6/2011 | Bernstein ................ A61L 9/042 239/44 |
| 2013/0276715 A1 | 10/2013 | Zirkiyev |
| 2014/0209700 A1* | 7/2014 | Olchovy ................... A61L 9/12 239/34 |

(Continued)

*Primary Examiner* — Ruth Ilan

(57) ABSTRACT

An air treating apparatus for a pet sanitary station, preferably an open, non-enclosed disposable cat litter box, and methods of liquid dosing and mounting said apparatus to an upper wall member integral or attached to the top of a vertical wall of the cat litter box. The apparatus comprises a moisture resistant, preferably paperboard blank folded approximately in-half forming a matchbook like folded apparatus having a top cover, bottom cover, opposing open sides, a convertible open and closing means, absorbent material attached to the bottom cover inside surface, three embodiments for liquid dosing the absorbent material whose fragrance or aroma permeates out said apparatus to treat the air above the cat litter and four embodiments for mounting said apparatus to the upper wall member. The invention includes methods to introduce the pet to a new fragrance, extend the useful life of used cat litter, mount, liquid dose the absorbent material, and open and close the apparatus.

12 Claims, 13 Drawing Sheets

(56) References Cited

U.S. PATENT DOCUMENTS

| | | | |
|---|---|---|---|
| 2015/0140054 A1* | 5/2015 | DiGregorio | A61L 9/12 424/411 |
| 2015/0245588 A1* | 9/2015 | Perorazio | A01K 1/0107 119/166 |
| 2016/0015848 A1* | 1/2016 | Jung | H05H 1/2406 422/121 |
| 2016/0030619 A1* | 2/2016 | Clark | A61L 9/12 206/575 |
| 2017/0209614 A1* | 7/2017 | Ramos | A61L 9/12 |

* cited by examiner

AIR TREATING APPARATUS FOR PET SANITARY STATION AND METHODS OF MOUNTING AND DOSING SAID APPARATUS

CROSS REFERENCE TO RELATED APPLICATIONS

Application No. 62/284,465
Filing Date: Oct. 1, 2015

U.S. Patent References Cited

Per attached USPTO Forms SB/08a

FIELD OF THE INVENTION

This invention relates to the field of pet sanitary stations and particularly to an air treating apparatus mounted to the top of a open, non-enclosed disposable cat litter box, where said apparatus is designed to receive doses of a liquid product whose evaporating fragrance or aroma treats the air above the cat litter.

DESCRIPTION OF PRIOR ART

Removing the unpleasant smell of a dirty cat litter box continues to plague pet owners. Products such as automated cat litter boxes, scoopable cat litter, deodorizing cat litter, scented cat litter and additives such as baking soda are some of the popular current remedies to remove the smell directly from within the cat litter. However, for cat owners who use these remedies, but do not change the basic litter and wash out and disinfect the cat pan, or cat pan attachments for up to a month, the unpleasant smell of dirty cat litter, dirty cat pan and attachments can permeate the entire room where the cat litter box is located.

Additional deodorizing remedies that work on the odor emanating from the dirty litter are aerosol sprays, gels, solid deodorizers and according to a manufacturer of furniture enclosures for cat litter boxes, a titanium dioxide (TiO2) coating applied to the interior walls of the enclosure in conjunction with a 24/7 blue light wave technology inside the enclosure. The problems with these products are: 1) the aerosols and sprays only deodorize the odors temporarily, 2) the gels and solid deodorizers are usually placed in the general vicinity of the cat litter box and their effectiveness is diluted, because they do not attack the smelly odors at the source, but only after the odors have already entered the room where the cat litter box is located, and 3) the TiO2 blue wave technology only works in totally enclosed cat litter boxes where many cats will not enter, and requires additional expense for the electricity to power the blue light 24/7, and the replacement costs for the blue light devices.

Only a few of the current air freshener and odor eliminator products are designed to be attached directly to the top of an open, non-enclosed cat litter box where they work continuously on the air above the dirty cat litter. There are two types of these devices, consisting of powered and non-powered. One such powered product is offered by The LitterMaid Company which is a fan that attaches vertically to the top of the cat litter box wall and draws the air from above the dirty cat litter through an activated charcoal screen to deodorize it. The problem with this method is the constant 24/7 use of electricity to power the fan, the constant noise of the fan and the height of the fan preventing the cat from entering the cat litter box where the fan is mounted. One such non-powered product is offered by Compac Industries with their Oma-Scent non-powered air freshener that hooks onto a vertical wall of an open, non-enclosed cat litter box and provides a deodorizing air freshener for the dirty cat litter. The problem with this product is that only the hook secured to the top of the vertical wall is near the top of the cat litter box, while the air freshener body hangs down vertically towards the floor on the outside of the cat litter box and away from the top of the cat litter box and the dirty cat litter where the dirty odors are emanating.

When we examine patents of an air treating apparatus mounted to the top of an open, non-enclosed cat litter box, where said apparatus is designed to receive doses of a liquid product whose evaporating fragrance or aroma will treat the air above the cat litter, I am not aware of existing prior art that uses a non-powered air treating apparatus that is designed to mount onto a horizontal or approximately horizontal upper wall member that is integral or attached to the top of a vertical wall of an open, non-enclosed cat litter box to treat the air above the cat litter.

U.S. Pat. No. 7,594,480, Deodorizer/Disinfectant Fluid Treatment System and Litter Liner for use therewith to Cressy, Sep. 29, 2009, uses a conduit strip within a cat pan liner to diffuse a disinfectant fluid into the cat litter where it is absorbed. This system is located under the litter, requires a powered source consisting of an Ozone Generator, which requires the extra expense of electricity to power the system, and it emits a noise related to the operating generator.

U.S. Pat. No. 5,289,800, Waste Odor Eliminator Cover for a Cat Waste Box, to Walton, Mar. 1, 1994, illustrates a dome mounted over a cat litter box with several slots in the dome ceiling that have charcoal filters to clear the warm fecal odor rising from the dirty cat litter as it rises into the cooler room air. This invention is not designed to use a liquid air freshener or liquid odor eliminator as the means to deodorize the dirty cat litter odor, but rather to use an enclosure to surround the cat litter box and direct by convection the warm fecal odors in the cat litter box upwards through the cleaning charcoal filters mounted in the top of the enclosure and out into the cool air of the room.

U.S. Pat. No. 5,220,885, Litter Box to Goetz, Jun. 22, 1993, uses an air freshener compartment in the upper ceiling section of a molded enclosed structure that houses a cat litter box. The air freshener deodorizes rising unpleasant odors from a dirty cat litter box as they rise to the enclosure's ceiling and escape through the slotted air freshener compartment into the room air. This invention is designed for a solid air freshener, because if the pet owner applied a liquid dose to an overhead absorbent material, the liquid could drip through the slots onto the cat.

U.S. Pat. No. 5,129,364, A One-Piece Disposable Cat Litter Box, to Randall, Jul. 14, 1992, illustrates a disposable cat litter box made from a single piece of cardboard with a charcoal filter mounted in the upper roof. This invention is designed to be a full enclosure disposable cat litter box and is not designed to deodorize the dirty cat litter odors using a liquid air freshener or liquid odor eliminator, but rather to clean the smelly air with charcoal filters as the air rises through the filters into the room.

U.S. Pat. No. 4,090,470, Litter Box to Williams, May 23, 1978, uses a deodorizing disinfecting element impregnated in an absorbent material that is within a housing underneath the cat litter box. Perforations in the housing allow the deodorizing disinfecting vapors to evaporate into the air. The problem with this invention is the housing that holds the absorbing material is underneath the cat litter box, which is hard to get at to replace or refresh, because you have to lift the litter box off a supporting structure and unscrew the housing to get at the absorbent material.

U.S. Pat. No. 3,872,832, Indoor Cat House to Quinn, Mar. 25, 1975, uses a furniture look alike enclosed structure for housing a cat litter box with a deodorizer mounted in the inside upper corner of the enclosure. This deodorizing structure would be difficult to change or refresh since it is inside of the enclosure up in the corner.

U.S. Pat. No. 3,793,989, Deodorized Pet Relief Station to Clark, Feb. 26, 1974, uses a mounted deodorizing structural assembly mounted to the end wall of an enclosed cat litter box where a wick receives deodorizing liquid from a container and disperses the air freshener fragrance within the enclosure. The problem with this invention is that the enclosure has to be taken apart to service the fragrance dispensing unit.

U.S. Pat. No. 3,428,026, Fumigated Pet House to Sohmers et al, February 1969, uses a deodorant tray mounted on the outside roof of the pet house to communicate with the interior roof through closely spaced holes in the floor of the tray. The tray enclosure prevents the cat from coming in contact with the deodorant form, while deodorant vapors evaporate into the enclosure through holes in the tray. The problem with this invention is that the pet owner has to manually remove the deodorant form from the deodorant tray to refresh the form and then return it to the tray permitting possible skin irritants in the deodorant to come in contact with the pet owners skin.

U.S. Pat. No. 1,384,866, Disinfecting Brooders to Silvers, Jul. 19, 1921, provides a liquid disinfectant reservoir in the roof of a brooder house. Vapors from the disinfectant evaporate and enter the brooder enclosure through elongated slots in the enclosure. This invention would be very dangerous for cats, because cats move around in an enclosure and hit the interior walls, which could agitate the liquid in the overhead reservoir and cause it to spill through the elongated slots down onto the cat.

Patent Application Publication #20130276715, Litter Box Guard to Zirkiyev, May 30, 2013, provides a housing in the top cover of an enclosed litter box where a sponge impregnated with a liquid or powder air freshener or deodorant will deodorize the room. This device provides no deodorizing of the air directly above the litter, but only after the unpleasant odor of the cat litter has already entered the room from the box entrance. Another device in the top-cover provides a holder for a liquid deodorant or air freshener impregnated sponge or charcoal filter to treat the odors rising up from the litter and through the device into the room. The problem with this invention is that a cat moving around inside the box could come in contact with the liquid in the sponge and get it on its fur and ingest the liquid from licking its fur, or licking the sponge.

In conclusion, insofar as I am aware the present invention provides a means for overcoming these prior art difficulties.

OBJECTS OF THE INVENTION

It is an object of the invention to provide a pet owner with an air treating apparatus mounted to a horizontal or approximately horizontal upper wall member that is integral or attached to the top of the vertical wall of an open, non-enclosed disposable cat litter box, where said apparatus comprises a match book like fold of preferably paperboard material, opposing open sides, top cover, bottom cover, absorbent material secured to a portion of the bottom cover, additional embodiment of a predetermined sized removal section in the top cover, additional embodiment of an access opening in the top cover, a convertible open and closing means, and a mounting means including additional embodiments to secure the apparatus to the horizontal or approximately horizontal upper wall member at the top of the vertical wall of a cat litter box.

It is an object of the invention to provide a pet owner with one or more air treating apparatuses mounted tangent to inwardly extending horizontal or approximately horizontal upper wall members that are integral or attached to the top of the vertical walls of an open, non-enclosed cat litter box, where said apparatuses will be positioned over opposing areas of the cat litter at the top of the cat litter box, enabling an evaporating fragrance or aroma from the liquid dosed absorbent material to permeate out the open sides of the air treating apparatuses to more effectively treat the air above the cat litter.

It is an object of the invention to provide a pet owner with an air treating apparatus mounted to said upper wall member of the cat litter box, where an absorbent material within said apparatus can be dosed daily, or when policing the cat litter box, or when needed, with a small amount of a liquid air freshener, or odor eliminating product whose evaporating fragrance will treat the air above the cat litter before the unpleasant odors of the dirty cat litter enter the room.

It is an object of the invention to provide the pet owner with an air treating apparatus mounted to said upper wall member of the cat litter box, where said apparatus can be dosed daily, or when policing the cat litter box, or when needed, with a small amount of a liquid cat attracting product whose evaporating aroma will treat the air above the cat litter to attract those cats who have poor sanitation habits to use the litter box instead of doing their business outside the litter box.

It is an object of the invention to provide the pet owner with an air treating apparatus mounted to said upper wall member of the cat litter box, where the absorbent material within said apparatus can be dosed daily, or when policing the cat litter box, or when needed, with a small amount of a liquid pet medicine whose evaporating aroma will treat the air above the cat litter to provide medicinal relief to the cat.

It is an object of the invention to provide the pet owner with an air treating apparatus incorporating quick and easy alternative mounting means comprising adhesives, hook-and-loop type male/female fastening tapes, or interlocking tab and slot devices to secure said apparatus to the top surface of the horizontal or approximately horizontal upper wall members that are integral or attached to the vertical walls of an open, non-enclosed cat litter box.

It is an object of the invention to provide the pet owner with an air treating apparatus mounted to said upper wall member of the cat litter box, where said apparatus is absent of any liquid product such as an air freshener, odor eliminator, cat attracting product, or pet medicine until the pet owner begins the dispensing onto the absorbent material within the apparatus of said liquid product whose evaporating fragrance or aroma treats the air above the cat litter.

It is an object of the invention to provide the pet owner with an air treating apparatus mounted to said upper wall member of the cat litter box, where said apparatus comprises a convertible open and closing means, whereby the pet owner can open the apparatus to dose the absorbent material with a small amount of a liquid product and then reclose the apparatus to prevent the pet from coming in contact with the liquid dosed absorbent material.

It is an object of the invention to provide the pet owner with an air treating apparatus mounted to said upper wall member of the cat litter box, where the top cover of said apparatus comprises an additional embodiment of a predetermined sized removable section that when removed provides an access opening in the top cover of the apparatus to enable the pet owner to dose the absorbent material within the apparatus with a small amount of a liquid product without having to open the apparatus when it is closed, and the opening allows the evaporating fragrance or aroma from the liquid dosed absorbent material to rise out through the opening to treat the air above the cat litter.

It is an object of the invention to provide the pet owner with an air treating apparatus mounted to said upper wall member of the cat litter box, where the top cover of said apparatus comprises said predetermined sized removable section that is designed to be removed after the pet, preferably a cat becomes familiar with the evaporating fragrance or aroma of the liquid product permeating out the open sides of the apparatus.

It is an object of the invention to provide the pet owner with an air treating apparatus mounted to said upper wall member of the cat litter box, where the top cover of said apparatus provides an additional embodiment of a predetermined sized access opening installed during manufacture to enable the pet owner to dose the absorbent material within the apparatus with a small amount of a liquid product without having to open the apparatus, and the opening allows the evaporating fragrance or aroma of the liquid product to rise out through the opening to treat the air above the cat litter.

It is an object of the invention to provide the pet owner with an air treating apparatus mounted to said upper wall member of the cat litter box, where the absorbent material within said apparatus can be dosed with the liquid product daily, or when policing the cat litter, or when needed, and the pet owner's liquid dosing regimen can be adjusted to enable the evaporating fragrance or aroma to be effective in treating the air above the cat litter until the cat litter is changed.

It is an object of the invention to provide the pet owner with air treating apparatuses mounted to the upper wall members of the cat litter box, where the pet owner can reduce the total cost for the cat litter by extending the uselife of the used cat litter before it has to be changed by dosing all the absorbent materials as needed within the mounted apparatuses with the liquid product whose evaporating fragrance will permeate out from all the apparatuses openings to eliminate the smelly odor of dirty cat litter.

It is an object of the invention to provide the pet owner with an air treating apparatus mounted to said upper wall member of the cat litter box, where the apparatus provides one or more moisture resistant barrier walls bordering one or more sides and bottom of the liquid dosed absorbent material to contain the liquid product within the absorbent material.

It is an object of the invention to provide the pet owner with an economical, non-powered air treating apparatus mounted to said upper wall member of the cat litter box, where said apparatus eliminates the electricity costs of powered units and the costs to replace the devices operated by the electricity.

It is an object of the invention to provide the pet owner with a quiet non-powered air treating apparatus mounted to said upper wall member of the cat litter box, where said apparatus eliminates the noise of powered units.

It is an object of the invention to provide the pet owner with one or more low profile apparatuses mounted to said upper wall members of the cat litter box, where said apparatuses do not interfere with the cat's entering and exiting the box from either end, or either side of the box.

It is an object of the invention to provide the pet owner with an apparatus mounting embodiment comprised of interlocking securing shaped slot devices to aid the pet owner in grasping the cat litter box upper wall member interlocking securing tab devices with two fingers.

It is an object of the invention to provide the pet owner with methods to easily and quickly refresh the absorbent material within the mounted apparatus with a small amount of a liquid product daily, or when policing the cat litter box, or when needed.

It is an object of the invention to provide the pet owner with a method to add an access opening in the top cover of the mounted apparatus to allow the evaporating fragrance or aroma from the liquid dosed absorbent material to rise out through said opening to treat the air above the cat litter It is an object of the invention to provide the pet owner with a method to supplement the evaporating fragrance or aroma from the liquid dosed absorbent material passing through the open sides of the air treating apparatus to treat the air above the cat litter by removing a predetermined sized removable section from the top cover of the apparatus, thus adding a top cover access opening to allow the fragrance or aroma from the liquid dosed absorbent material to also rise out through the top opening to treat the air above the cat litter.

It is an object of the invention to provide methods to secure one or more air treating apparatuses during manufacture to one or more upper wall members of the cat litter box to eliminate installation time by the pet owner.

It is an object of the invention to provide the pet owner with methods to easily and quickly mount one or more apparatuses to said upper wall members of the cat litter box.

It is an object of the invention to provide the pet owner with a method to open and close the mounted apparatus, whereby the pet owner can open the apparatus to remove the predetermined sized removable section from the top cover, or dose the absorbent material with a small amount of a liquid product and then reclose the apparatus to prevent the cat from coming in contact with the liquid dosed absorbent material.

It is an object of the invention to provide the pet owner with a method to gently introduce the pet, preferably a cat to a new evaporating fragrance or aroma of a liquid product within the air treating apparatus mounted to said upper wall member of the open, non-enclosed cat litter box.

It is an object of the invention to provide the pet owner with an air treating apparatus mounted to said upper wall member of the cat litter box, where the pet owner does not have to open the apparatus to service it.

It is an object of the invention to be of minimal expense and as such can be used in a complete disposable fashion.

SUMMARY OF THE INVENTION

A non-powered matchbook like folded and closed air treating apparatus mounted to the top of an open, non-enclosed cat litter box where said apparatus is designed to receive doses of a liquid product whose evaporating fragrance or aroma will treat the air above the cat litter.

The apparatus comprises a predetermined sized preferably paperboard blank of material with a transverse fold-line crease across the approximate longitudinal center of the blank to enable the blank to be folded approximately in-half into a matchbook like folded apparatus having a top horizontal cover and a bottom horizontal cover with the closed end of the apparatus at the folded end and the open end at the opposing end. The apparatus has a predetermined sized absorbent material capable of holding liquid doses secured to a predetermined section of the inside surface of the bottom cover. The absorbent material is absent of any liquid product until the pet owner begins to dispense a liquid product onto the absorbent material. The paperboard material comprises a moisture resistant surface tangent to the absorbent material.

The invention comprises at least four mounting means to secure the apparatus to the upper wall member of the cat litter box, comprising: 1) an adhering substance such as an adhesive attached to a predetermined section of the underside surface of said bottom cover that is tangent to a horizontal or approximately horizontal upper wall member of the cat litter box to mount said apparatus to the upper wall member at the top of the cat litter box, 2) an adhering substance such as an adhesive attached to a predetermined section of the upper wall member surface that is tangent to the underside surface of the apparatus bottom cover to mount said apparatus to the top of the upper wall member of the cat litter box, 3) an adhering substance such as a hook-and-loop-type male/female fastening tape attached to a predetermined section of the underside surface of said bottom cover adapted to interlock with an opposing Velcro-type male/female fastening tape attached to the upper wall member to mount said apparatus tangent to the predetermined section of the upper wall member, and 4) one or more bottom cover interlocking securing shaped slot devices and one or more upper wall member interlocking securing tabs devices adapted to interlock with respect to one another to mount the apparatus to the upper wall member. One or more apparatuses are secured to one or more upper wall members that are integral or attached to the top of the vertical walls of the open, non-enclosed cat litter box.

A convertible open and closing means to both open and close said apparatus at the open end comprising at least one opening and closing device integral to the top cover and at least one opposing opening and closing device integral to the bottom cover adapted to unlock and interlock with respect to one another at said open end, whereby the apparatus when interlocked and closed prevents pets, preferably cats from coming in contact with the absorbent material, and when opened allows the absorbent material to be dosed with the liquid. Alternate embodiments for dosing the absorbent material within the apparatus, comprise a predetermined sized removable section in a predetermined section of the horizontal top cover that when removed provides an access opening in the top cover to dose the absorbent material with a liquid without having to open the closed apparatus, and a predetermined sized opening in a predetermined section of the top cover installed during manufacture enabling the absorbent material to be dosed with a liquid product without opening the closed apparatus. Both liquid dosed embodiments add an opening to the top cover that supplements the evaporating fragrance or aroma coming out the open sides of the apparatus by also allowing the evaporating fragrance or aroma to rise out through the top cover opening to treat the air above the cat litter.

The closed apparatus mounted to the top of the cat litter box is less than one inch high, whereby the apparatus does not interfere with the cat's entering or exiting the cat litter box.

The invention includes methods to mount the apparatus parallel and tangent to the upper wall member that is integral or attached to the top of the vertical wall of the open, non-enclosed cat litter box. The invention includes methods to manually dose the absorbent material within the apparatus with a liquid product. The invention includes a method to open and close the apparatus. The invention includes a method to gently introduce a pet, preferably a cat to a new or different fragrance or aroma evaporating from the liquid dosed absorbent material. The invention includes a method of increasing the amount of fragrance or aroma from the air treating apparatus. The invention includes a method to reduce the total cost of the cat litter by extending the useful life of the cat litter before the litter has to be changed. The invention includes methods to mount one or more air treating apparatuses during manufacture to one or more upper wall members of the cat litter box to eliminate installation time by the pet owner.

DESCRIPTION OF THE SPECIFICATIONS

Figure 1:
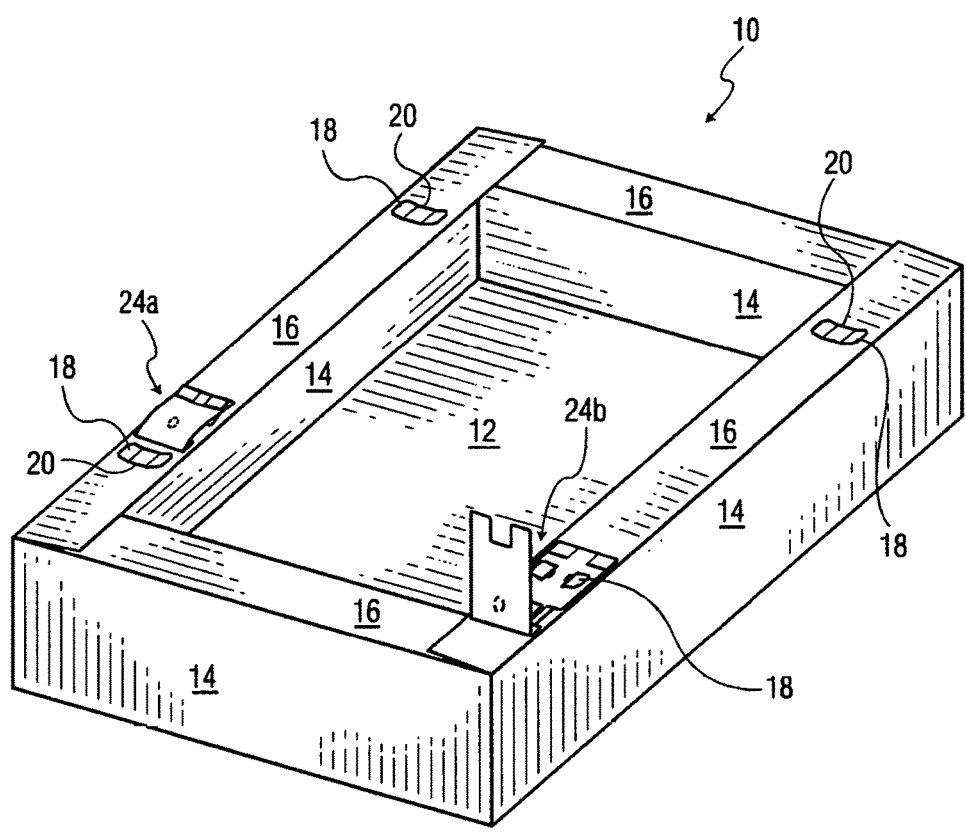
FIG. 1—A Non-Enclosed Cat Litter Box with Mounted Air Treating Apparatuses

FIG. 1 illustrates an open, non-enclosed disposable cat litter box 10 having a horizontal bottom wall 12, a plurality of vertical walls 14, a plurality of horizontal or approximately horizontal upper wall members 16, that are integral or attached to the top of the vertical walls 14, and extend inwardly for an extended length over the horizontal bottom wall 12, a plurality of upper wall members interlocking securing tab devices 18 and a plurality of upper wall member interlocking securing slot devices 20 adapted to interlock with respect to one another to form the open, non-enclosed cat litter box 10. FIG. 1, also illustrates an air treating apparatus 24*a* comprising an adhering substance (not shown) to mount it to the upper wall member 16 and air treating apparatus 24*b* comprising bottom cover interlocking securing slot devices 48 interlocked with the upper wall member interlocking securing tab devices 18 to mount air treating apparatus 24*b* to the upper wall member 16 of cat litter box 10.

Figure 2:
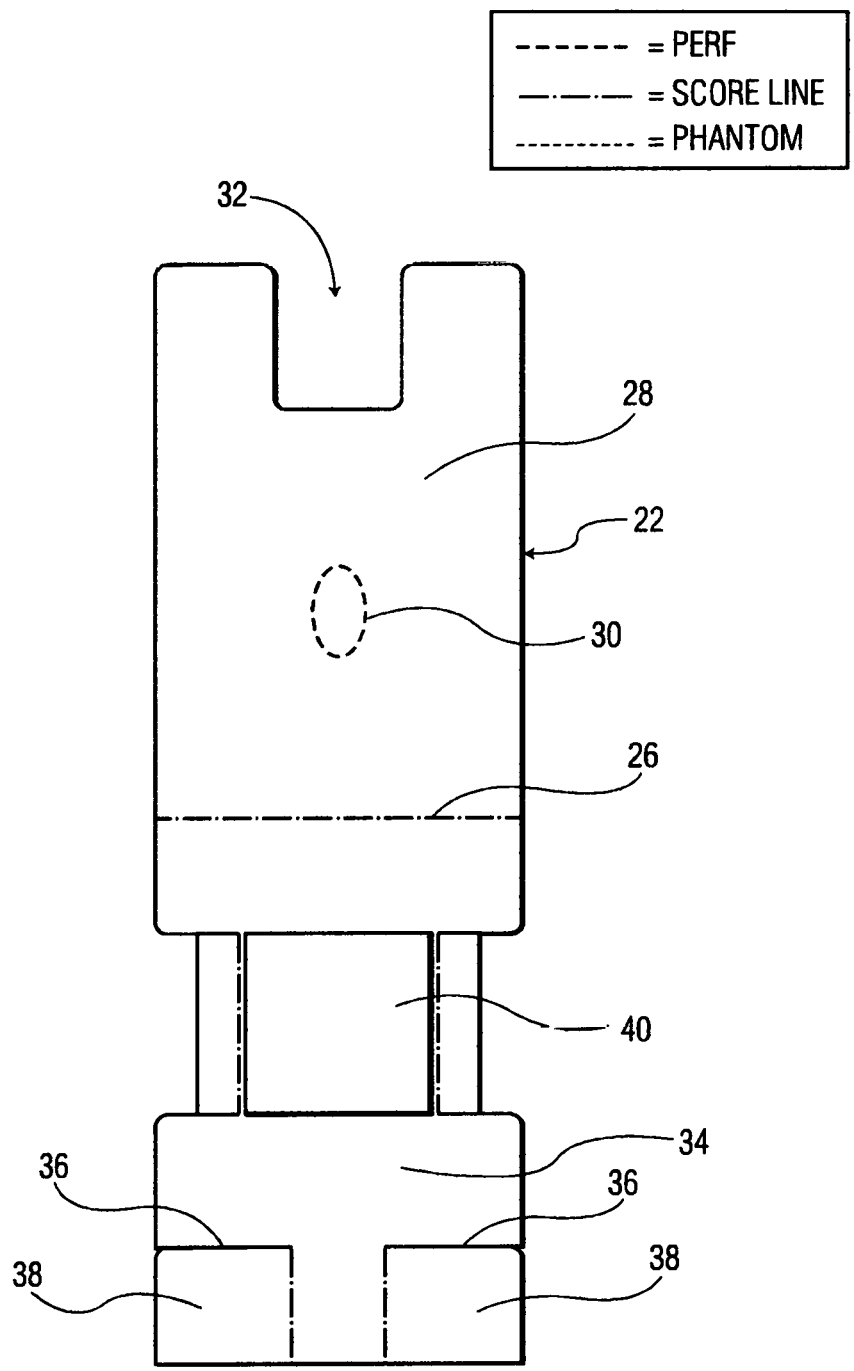
FIG. 2—Top-View of Apparatus Paperboard Blank

FIG. 2 illustrates a top-view of a one-piece die-cut and fold-line creased, moisture resistant paperboard blank 22, before being folded into a matchbook like air treating apparatus 24*a* (folded apparatus not shown) with a transverse fold-line crease 26 scored across the approximate longitudinal center of blank 22. Said blank 22 when folded along transverse fold-line crease 26 comprises a top-cover 28 with a predetermined sized removable section 30 and a pre-determined sized convertible open and closing slot device 32, a bottom cover 34 including convertible open and closing pre-determined sized die-cut slits 36 and pre-determined sized convertible open and closing tabs devices 38. A predetermined sized absorbent material 40 is secured to a predetermined sized section of the inside surface of the bottom cover 34.

Figure 3:
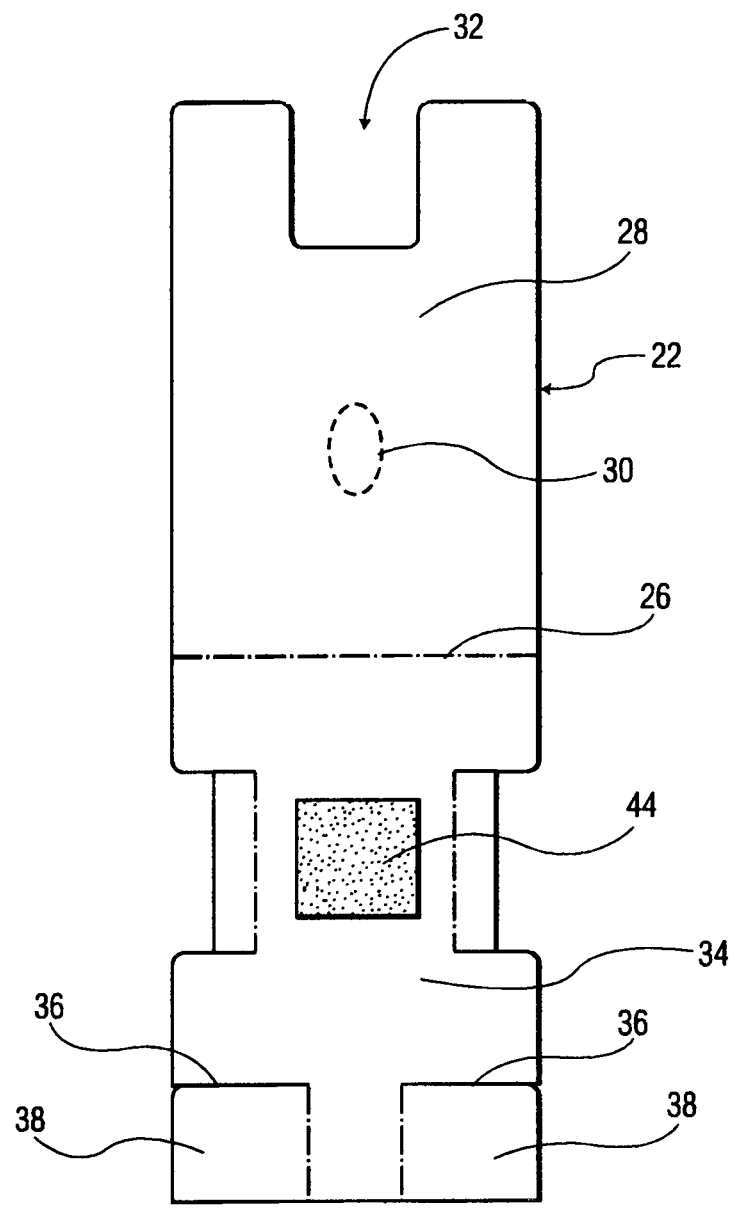
FIG. 3—Bottom View of Apparatus Paperboard Blank

FIG. 3, illustrates the bottom-view of FIG. 2, with an adhering substance 44 such as an adhesive or hook-and-loop-type male/female fastening tape attached to a predetermined section of the bottom cover 34.

Figure 4:
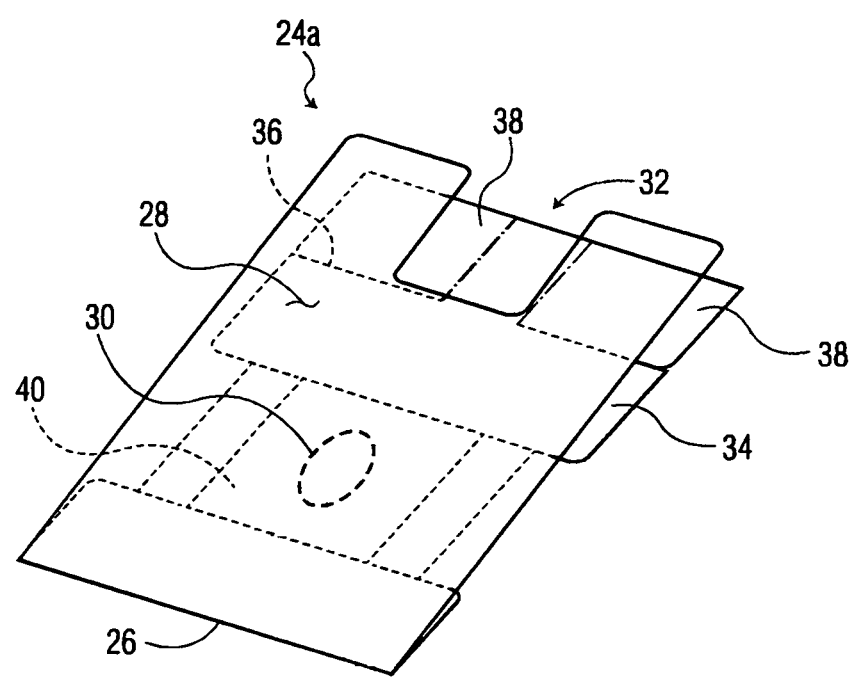
FIG. 4—Blank Folded Approximately In-Half into Matchbook-Like fold

FIG. 4, illustrates FIGS. 2 and 3, blank 22 folded approximately in-half along transverse fold-line crease 26 to form a matchbook like folded air treating apparatus 24a having a top cover 28 and a bottom cover 34 with the closed end of the folded apparatus 24a at the folded end and the open end of folded apparatus 24a at the opposite end.

Figure 5:
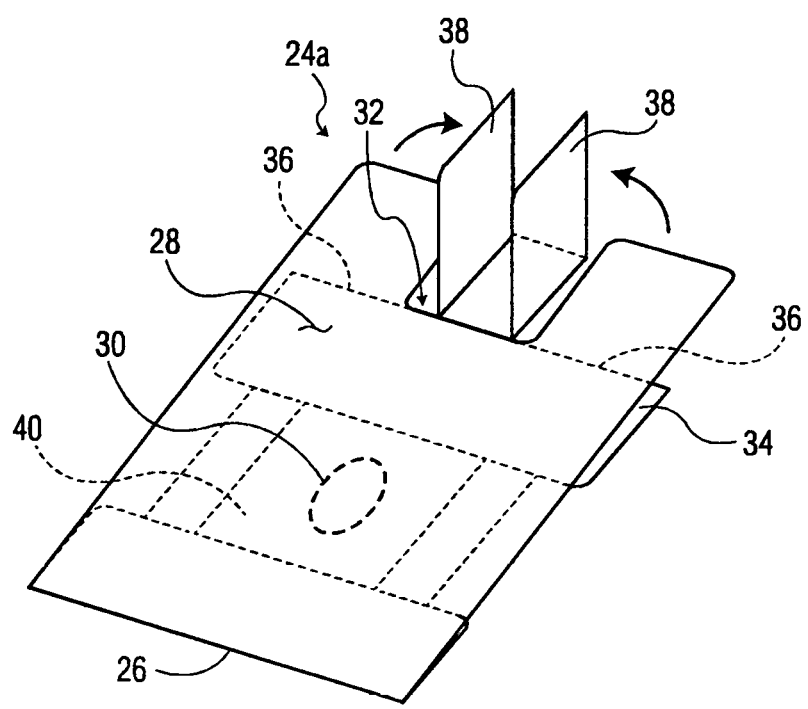
FIG. 5—Method of Folding & Inserting Open & Closing Apparatus Tab Devices

FIG. 5, illustrates FIG. 4, and the method said air treating apparatus 24a bottom cover 34 convertible open and closing tab devices 38 are folded vertically by the pet owner and inserted into the top cover 28 convertible open and closing slot device 32.

Figure 6:
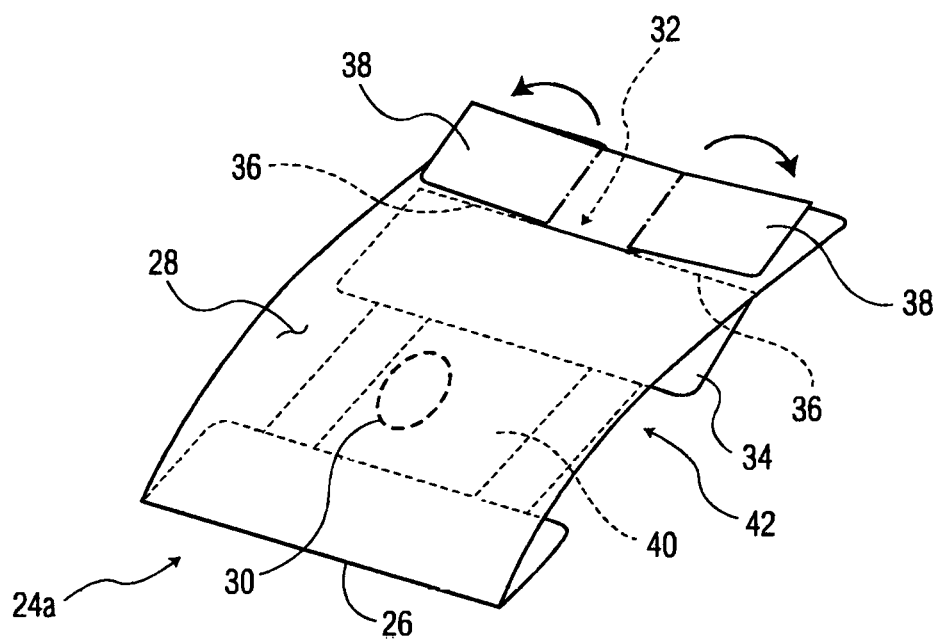
FIG. 6—Method of Locking Open & Closing Apparatus Tab Devices

FIG. 6, illustrates FIG. 5 and the method said air treating apparatus 24a bottom cover 34 convertible open and closing tab devices 38 are folded by the pet owner into a horizontal interlocking position on the outside surface of top cover 28 to interlock and close top cover 28 to the bottom cover 34, and closing of apparatus 24a and illustrating the open sides 42 of the closed apparatus 24a.

Figure 7:
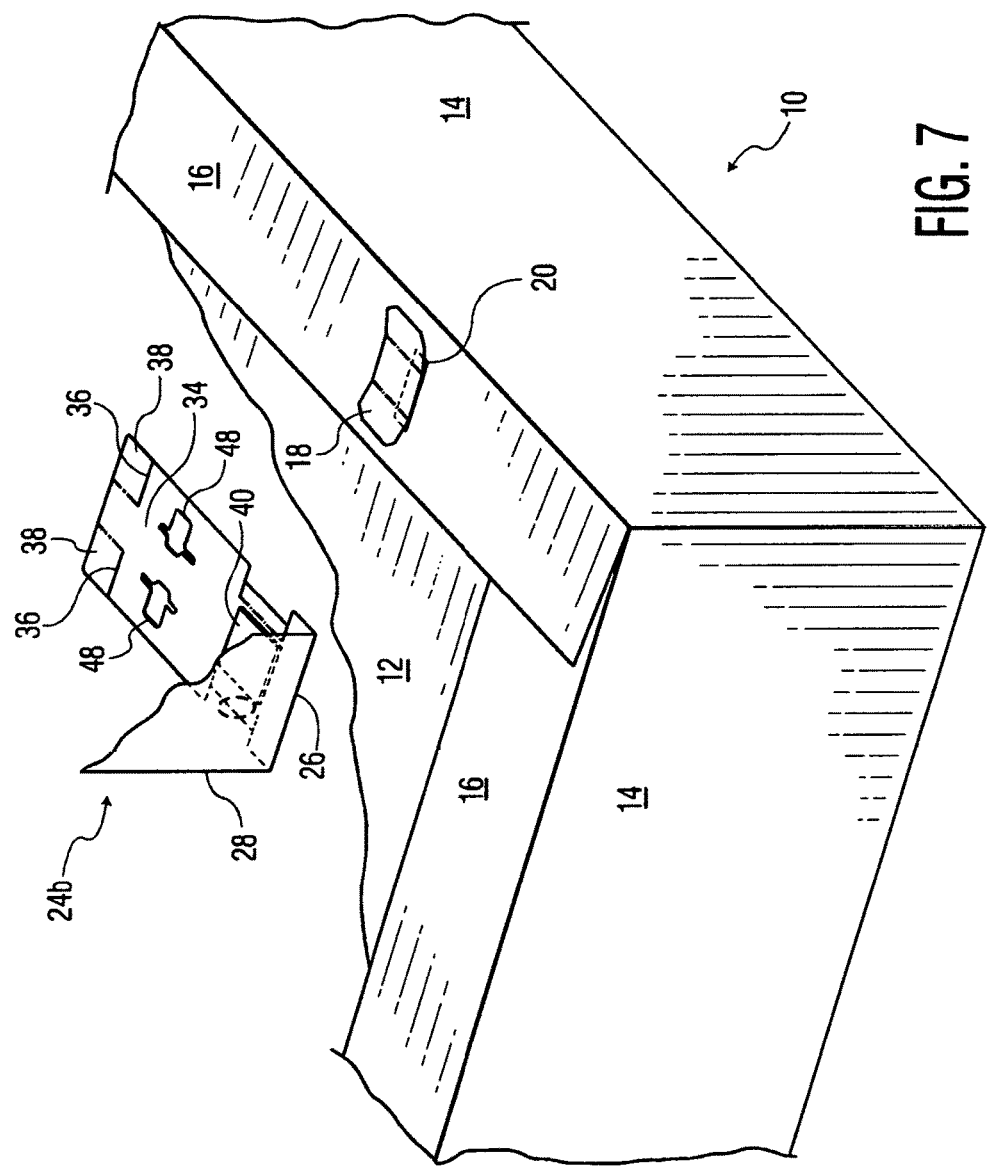
FIG. 7—Preparing to Mount Open Apparatus to Cat Litter Box

FIG. 7, illustrates the fourth embodiment to mount the open air treating apparatus 24b to upper wall member 16 comprising one or more bottom cover interlocking securing slot devices 48 and one or more upper wall member interlocking securing tab devices 18 that will be adapted to interlock with respect to one another to mount said apparatus 24b to the top of upper wall member 16 of the open, non-enclosed cat litter box 10. The bottom cover interlocking securing slot devices 48 further comprise predetermined sized shaped slots to enable two fingers to grasp the upper wall member 16 interlocking securing tab devices 18 to aid in the insertion of the interlocking securing tab devices 18 within the open apparatus 24b.

Figure 8:
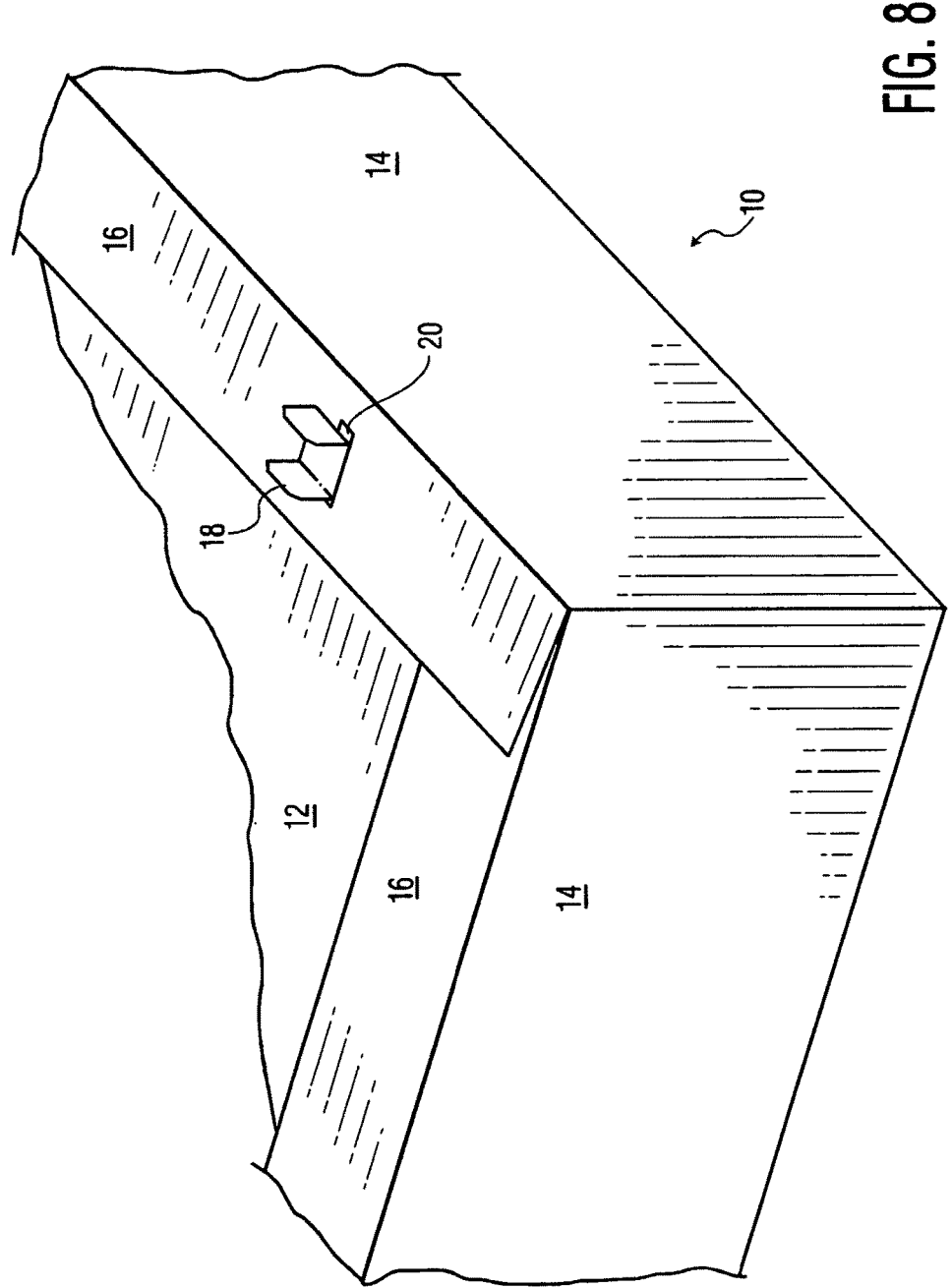
FIG. 8—Method to Fold Vertical Cat Litter Box Interlocking Securing Tab Devices

FIG. 8 illustrates the method by which the upper wall member 16 interlocking securing tab devices 18 are folded by the pet owner into an approximately vertical unlock position prior to inserting into the bottom cover 34 interlocking securing shaped slot devices 48 of said air treating apparatus 24b (not shown).

Figure 9:
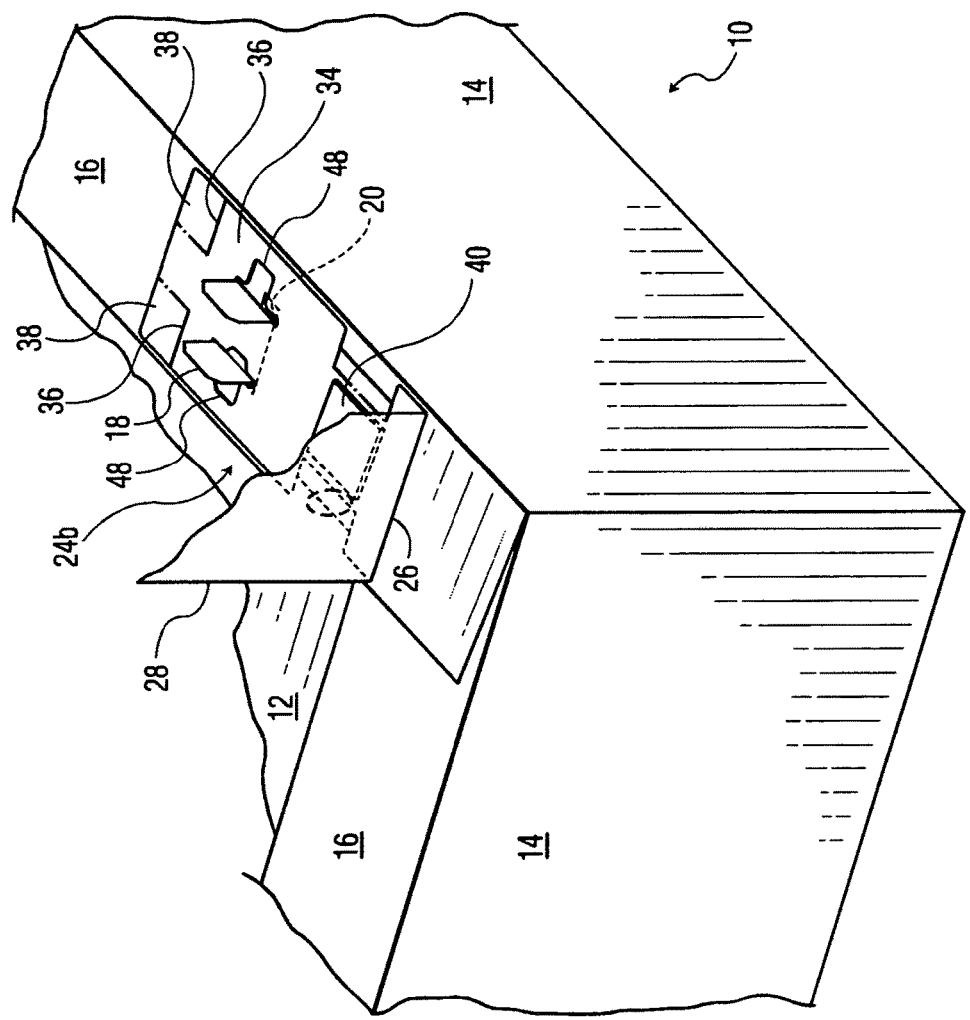
FIG. 9—Method To Insert Interlocking Securing Tab Devices into Open Apparatus

FIG. 9, illustrates the method by which the approximately vertical interlocking securing tab devices 18 of upper wall member 16 are inserted into the apparatus 24b bottom cover 34 interlocking securing shaped slot devices 48 when apparatus 24b is mounted parallel and tangent to upper wall member 16.

Figure 10:
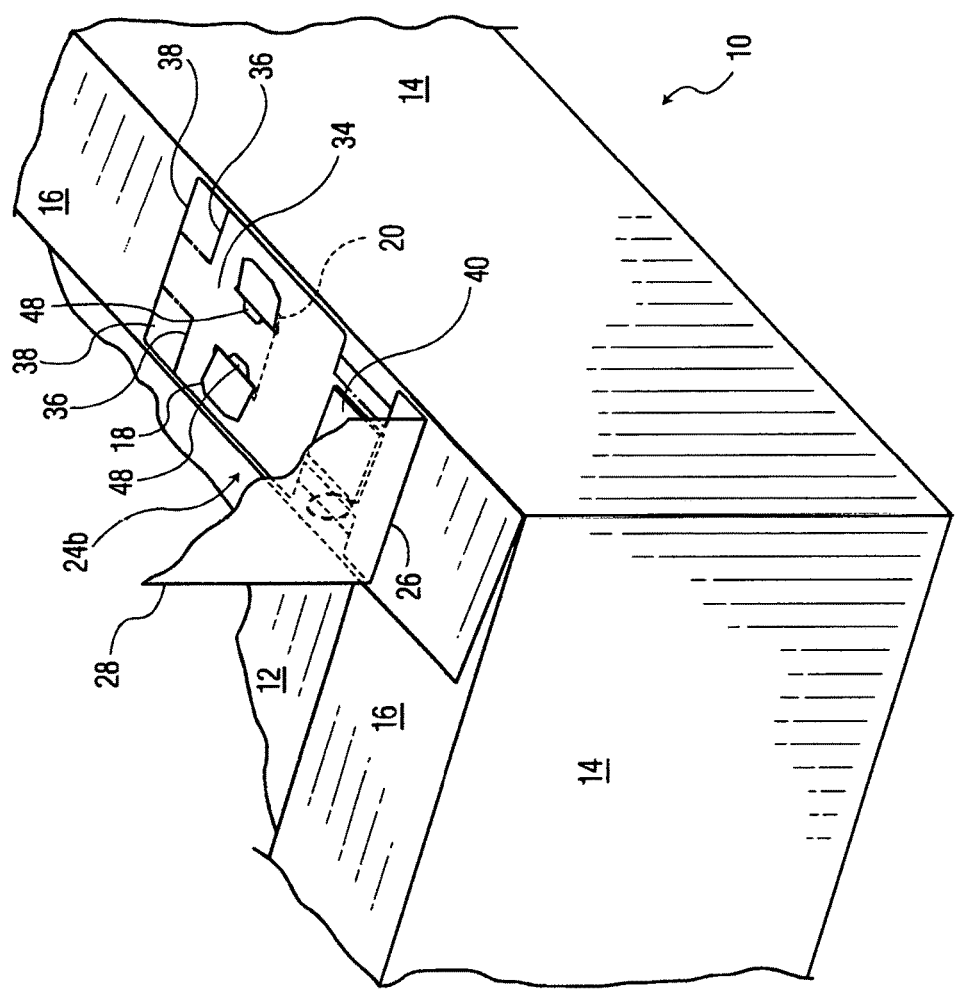
FIG. 10—Method of Locking Open Apparatus to Cat Litter Box

FIG. 10, illustrates the method by which the inserted upper wall member 16 approximately vertical oriented interlocking securing tab devices 18 illustrated in FIG. 9, are folded into the horizontal interlocking position on the inside surface of bottom cover 34 of apparatus 24b to lock apparatus 24b parallel and tangent to upper wall member 16.

Figure 11:
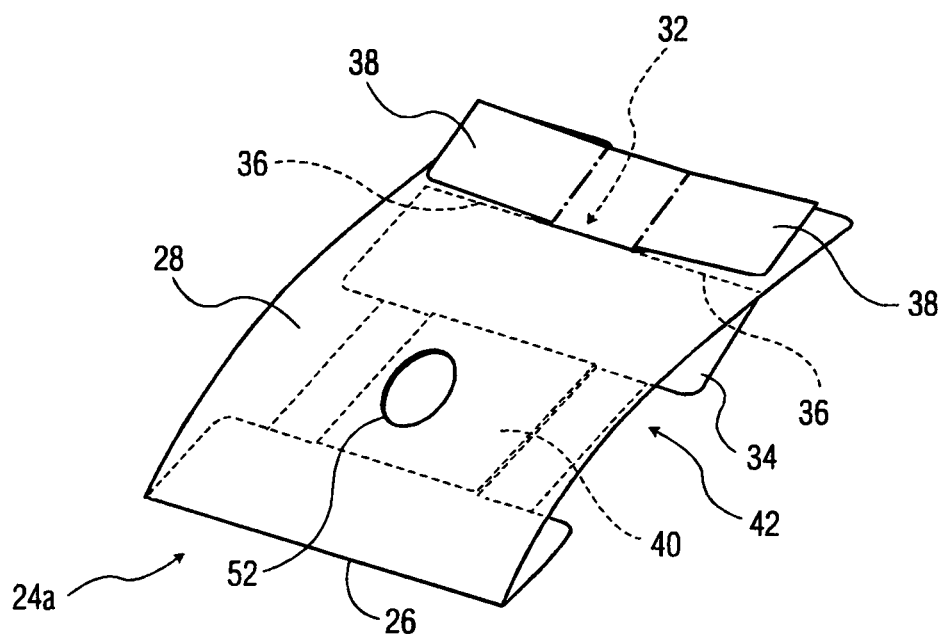
FIG. 11—Access Opening in Apparatus Top Cover Installed During Manufacture

FIG. 11, illustrates the closed air treating apparatus 24a having a predetermined section of the top cover 28 comprising a predetermined sized access opening 52, installed during manufacture whereby when the apparatus is closed, the opening allows access to dose the absorbent material 40 with the liquid product without having to open the closed apparatus 24a.

Figure 12:
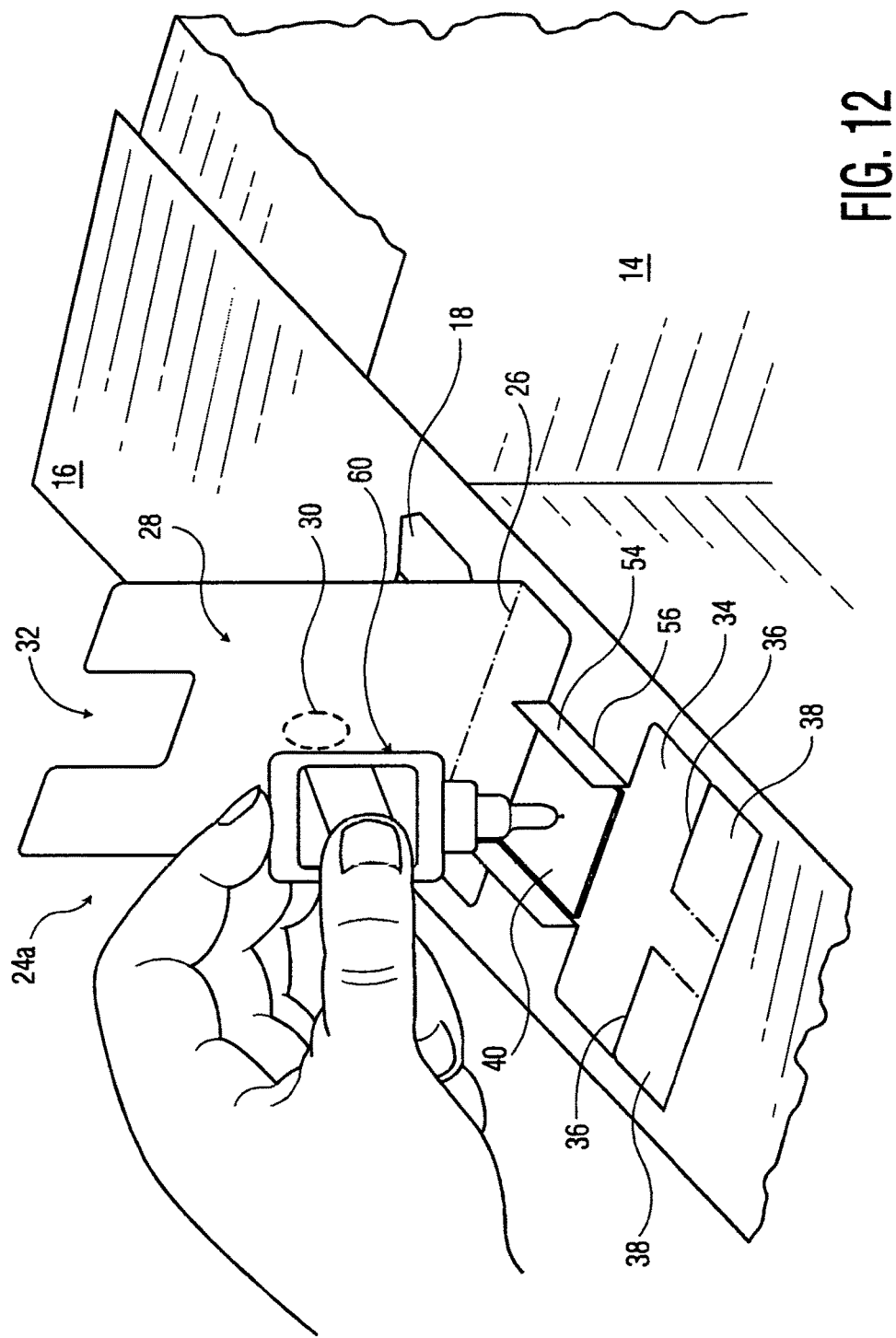
FIG. 12—Method of Liquid Dosing Absorbent Material in Open Apparatus

FIG. 12, illustrates the air treating apparatus 24a wherein one or more horizontal bottom cover members 54 connected along longitudinal fold-line creases 56 to said horizontal bottom cover 34 are folded approximately vertically to said horizontal bottom cover 34 along said creases 56 and have an extended length and height approximately tangent to one or more sides of the absorbent material 40, whereby said folded bottom cover members 54 act as a barrier wall bordering the absorbent material 40 to contain doses of the liquid product within the absorbent material 40. FIG. 12, also illustrates the method of liquid dosing the absorbent material 40 of open apparatus 24a by using a container 60 preferably a plastic squeeze dropper bottle container to dispense one or more doses of a liquid product onto the absorbent material 40 when the top cover 28 of apparatus 24a is raised approximately perpendicular to the bottom cover 34 of apparatus 24a exposing absorbent material 40 while apparatus 24a is mounted to the upper wall member 16 of cat litter box 10.

Figure 13:
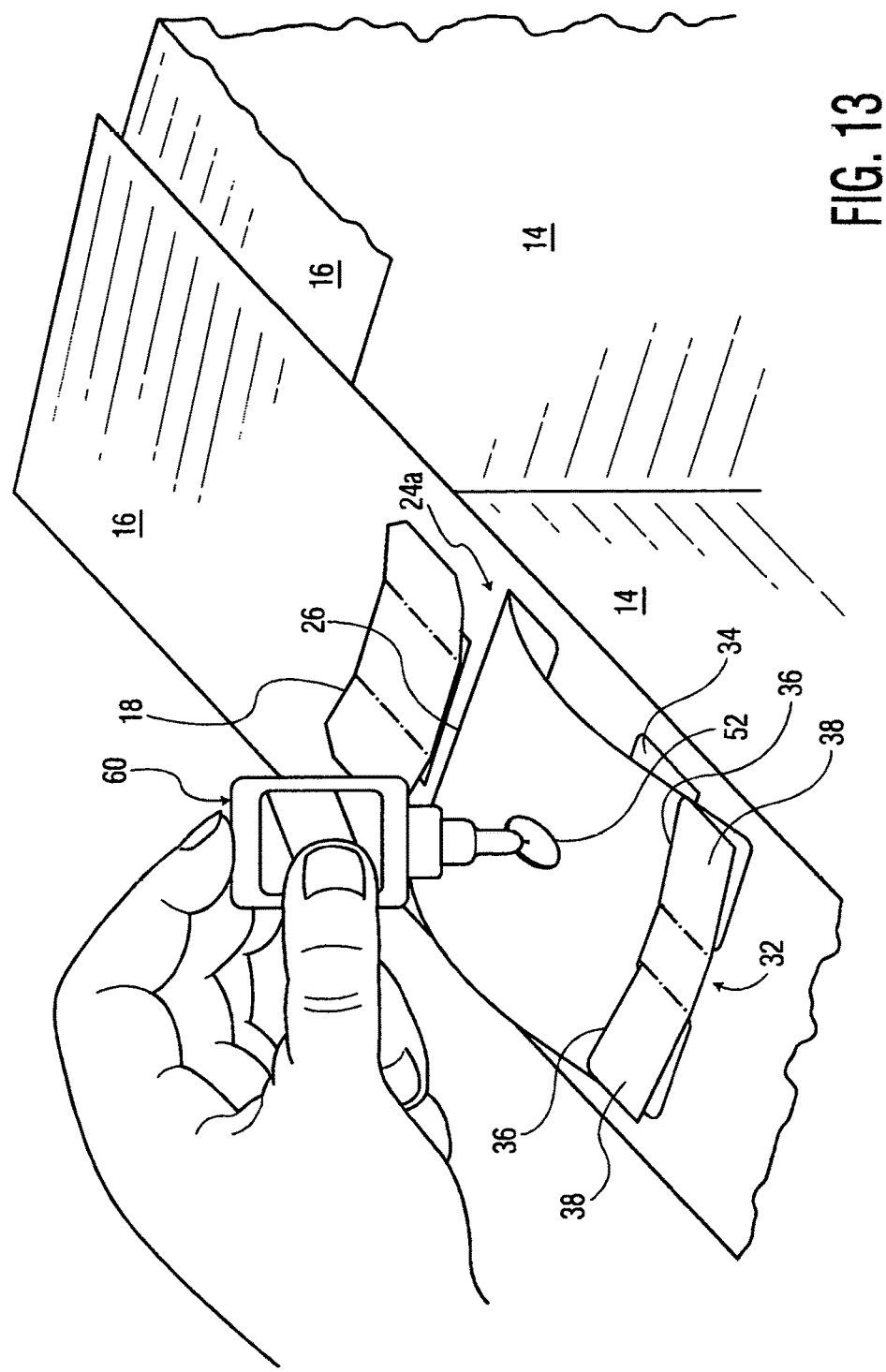
FIG. 13—Method of Liquid Dosing Absorbent Material in Closed Apparatus

FIG. 13, illustrates apparatus 24a mounted to the upper wall member 16 of cat litter box 10, and the method of liquid dosing the absorbent material 40 of closed apparatus 24a after the predetermined sized removable section 30 (not shown) of top cover 28 has been removed by the pet owner creating the predetermined sized access opening 52, whereby the pet owner can dose the absorbent material 40 within apparatus 24a through access opening 52 with a liquid product from container 60 without having to open apparatus 24a.

The invention claimed is:

1. An air treating apparatus for an open, non-enclosed disposable cat litter box comprising:
    (a) a one-piece, predetermined sized, flat blank of foldable, material;
    (b) said blank having a transverse fold-line across the approximate center of the blank, whereby said blank is folded approximately in-half along said fold-line into a matchbook like folded apparatus with a folded end and an open end;
    (c) said matchbook like folded apparatus having a top horizontal cover and a bottom horizontal cover with the closed end at the folded end and the open end at an opposite end;
    (d) said matchbook like folded apparatus having a predetermined sized absorbent material secured to a predetermined section of an inside surface of the horizontal bottom cover;
    (e) said absorbent material is capable of holding liquid doses;
    (f) said matchbook like folded apparatus is mounted tangent to the top of a horizontal or approximately horizontal upper wall member that is integral or attached to the top of a vertical wall of the open, non-enclosed cat litter box;
    (g) said matchbook like folded apparatus mounted parallel and tangent to the top of the horizontal or approximately horizontal upper wall member comprises a convertible opening and dosing means having an interlocking securing slot in said top cover adapted to interlock with interlocking securing tabs in the bottom cover to both open and close said apparatus at the open end of the apparatus, whereby the apparatus when unlocked and opened allows the absorbent material to be dosed with a liquid product and when closed prevents a pet from coming in contact with the absorbent material;

(h) said matchbook like folded and closed apparatus mounted parallel and tangent to the top of the upper wall member comprises opposing open sides, whereby room air passing through the open sides transports an evaporating fragrance or aroma from the liquid dosed absorbent material out over the cat litter to treat the air above the cat litter.

2. The air treating apparatus for an open, non-enclosed disposable cat litter box of claim 1, wherein the matchbook like folded and closed apparatus is mounted to the top of the upper wall member by an adhering adhesive attached to a predetermined underside surface of said bottom cover.

3. The air treating apparatus for an open, non-enclosed disposable cat litter box of claim 1, wherein the matchbook like folded and closed apparatus is mounted to the top of the upper wall member by an adhering adhesive attached to a predetermined section of the upper wall member surface that is tangent to a predetermined section of an underside surface of the apparatus bottom cover.

4. The air treating apparatus for an open, non-enclosed disposable cat litter box of claim 1, wherein the matchbook like folded and closed apparatus is mounted to the top of the upper wall member by a hook-and-loop male/female fastening tape attached to a predetermined section of the upper wall member surface and adapted to interlock with an opposing hook-and-loop male/female fastening tape attached to an underside surface of the apparatus bottom cover.

5. The air treating apparatus for an open, non-enclosed disposable cat litter box of claim 1, wherein said matchbook like folded apparatus is mounted to the top of the upper wall member by one or more predetermined sized interlocking securing slot devices in a predetermined section of the bottom cover adapted to interlock with one or more integral predetermined sized interlocking securing tab device of the upper wall member when said matchbook like folded apparatus is open.

6. The air treating apparatus for an open, non-enclosed disposable cat litter box of claim 5, wherein, when open, said matchbook like folded apparatus comprises predetermined sized interlocking securing slot devices, wherein the slots further comprise predetermined sized shapes configured to enable two fingers to grasp the interlocking securing tab devices at the interlocking securing shaped slot devices to aid in the insertion of the interlocking securing tab devices within an inside surface of the open apparatus bottom cover.

7. The air treating apparatus for an open, non-enclosed disposable cat litter box of claim 1, wherein a predetermined section of said horizontal top cover comprises a predetermined sized removable section of the top cover, whereby when said matchbook like folded apparatus is closed the removed section allows an access opening in the top cover to dose the absorbent material with a liquid without having to open the matchbook like folded apparatus.

8. The air treating apparatus for an open, non-enclosed disposable cat litter box of claim 1, wherein a predetermined section of said horizontal top cover comprises a predetermined sized opening installed during manufacture, whereby when said matchbook like folded apparatus is closed the opening allows access to dose the absorbent material with a liquid without having to open the matchbook like folded apparatus.

9. The air treating apparatus for an open, non-enclosed disposable cat litter box of claim 1, further comprising one or more horizontal bottom cover members having an extended length and height and connected along longitudinal fold-line creases to said horizontal bottom cover, whereby when said bottom cover members are folded approximately vertically to said horizontal bottom cover along said fold-line crease, the folded vertical bottom cover members act as a barrier wall bordering the absorbent material to contain doses of the liquid product within the absorbent material.

10. The air treating apparatus for an open, non-enclosed disposable cat litter box of claim 1, wherein said horizontal or approximately horizontal upper wall member includes a plurality of upper wall members that extend inwardly for an extended length over the open, non-enclosed cat litter box.

11. The air treating apparatus for an open, non-enclosed disposable cat litter box of claim 1, wherein when said matchbook-like folded apparatus is closed it is less than one inch high, whereby the closed apparatus does not interfere with the pet's entering or exiting the cat litter box.

12. The air treating apparatus for an open, non-enclosed disposable cat litter box of claim 1, wherein the matchbook-like folded apparatus comprises a paperboard material and a moisture resistant surface tangent to the absorbent material.

* * * * *